(12) United States Patent
Fried

(10) Patent No.: US 9,173,764 B2
(45) Date of Patent: Nov. 3, 2015

(54) SPLINT CONFIGURED TO PROVIDE SUPPORT, GENTLE MASSAGE, AND FRICTIONAL HEAT DURING USE AND METHOD OF MANUFACTURE

(71) Applicant: Scott Fried, Gwynedd Valley, PA (US)

(72) Inventor: Scott Fried, Gwynedd Valley, PA (US)

( * ) Notice: Subject to any disclaimer, the term of this patent is extended or adjusted under 35 U.S.C. 154(b) by 146 days.

(21) Appl. No.: 14/158,088

(22) Filed: Jan. 17, 2014

(65) Prior Publication Data

US 2015/0018738 A1    Jan. 15, 2015

Related U.S. Application Data

(60) Provisional application No. 61/813,408, filed on Apr. 18, 2013.

(51) Int. Cl.
*A61F 5/00* (2006.01)
*A61F 5/01* (2006.01)

(52) U.S. Cl.
CPC .................... *A61F 5/013* (2013.01)

(58) Field of Classification Search
CPC .............. A61F 2007/0024; A61F 2007/0086; A61F 2007/009; A61F 2007/0093; A61F 2007/0096; A61F 2007/0228; A61F 2220/0025; A61F 2250/001; A61F 5/0104; A61F 5/0123; A61F 5/0127; A61F 5/013; A61F 5/05866; A61F 5/0118; G03G 13/16; G03G 7/00; G03G 15/161; G03G 15/1625; G03G 15/1695; G03G 7/0053; G03G 7/008; G03G 7/0086; B29C 43/28; B29C 47/0014; B29C 47/02; B29C 63/06; B29C 65/344; A63B 21/026; A63B 21/1449; A63B 23/16
USPC .............................. 602/20–23; 128/878–897
See application file for complete search history.

(56) References Cited

U.S. PATENT DOCUMENTS

| | | | | |
|---|---|---|---|---|
| 6,517,501 | B1 * | 2/2003 | Slautterback | 602/5 |
| 6,740,056 | B2 * | 5/2004 | Slautterback | 602/21 |
| 2004/0049141 | A1 * | 3/2004 | Slautterback et al. | 602/21 |
| 2008/0249446 | A1 * | 10/2008 | Baumgartner et al. | 602/7 |

* cited by examiner

*Primary Examiner* — Michael Brown
(74) *Attorney, Agent, or Firm* — Garcia-Zamor IP Law; Ruy M. Garcia-Zamor

(57) ABSTRACT

A splint which preferably gives support, proper neutral positioning of the wrist and which allows freedom of motion for activities.

17 Claims, 14 Drawing Sheets

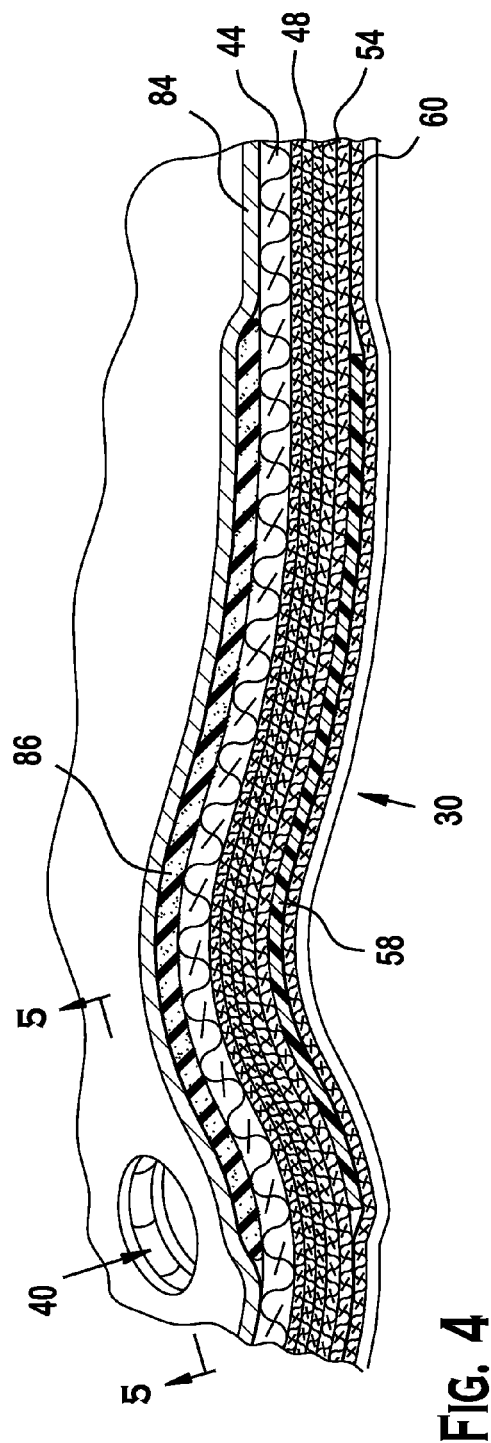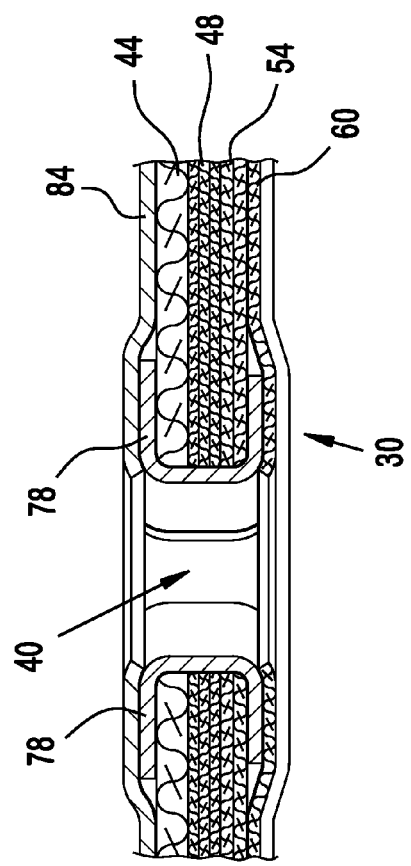

SPLINT CONFIGURED TO PROVIDE SUPPORT, GENTLE MASSAGE, AND FRICTIONAL HEAT DURING USE AND METHOD OF MANUFACTURE

This application claims priority to and benefit of the following U.S. patent application: U.S. Provisional Patent Application 61/813,408, filed Apr. 18, 2013, which is hereby incorporated by reference herein as if fully set forth in its entirety.

BACKGROUND

Prior art splints are not suitable for maximally treating carpal tunnel and tendinitis at the wrist. Prior art splints are not correct physiologically to treat these hand and wrist disorders effectively. Most prior art splints place the wrist and an extended or cock up position. Others are either too rigid or do not offer enough support.

It may be advantageous to provide a splint and a method of manufacturing a splint, that is more effective in treatment of carpal tunnel and tendonitis in the wrist, that may be physiologic, may be customizable to fit a user like a glove, and/or that may be customized to the wearer's hand and wrist to facilitate healing and recovery from injuries or disorders.

SUMMARY

In one aspect, a preferred method of the present invention is used for manufacturing a custom splint adapted for a person configured for use on a hand, a wrist, and a forearm of the person. The method including the steps of: applying a stockinette to the wrist and the forearm, the stockinette being configured to form a first layer of the splint; wrapping a fabric material about the first layer of the splint to form a second layer of the splint configured to provide bulk to the splint and to protect the wrist and the forearm of the person covered by the splint; while maintaining a neutral position of the wrist, wrapping a semi-elastic woven stretch material around the second layer of the splint to form a third layer of the splint configured to provide spring and breathability to the splint; and positioning a reinforcement strut on the third layer and securing the reinforcement strut thereto proximate to the wrist such that the reinforcement strut is configured to facilitate maintaining the wrist in a neutral position.

In another aspect, a preferred method of the present invention provides a custom splint adapted for a person configured for use on a hand, a wrist, and a forearm of the person. The method including the steps of: applying a stockinette to the wrist and the forearm, the stockinette being configured to form a first layer of the splint; wrapping a fabric material about the first layer of the splint to form a second layer of the splint configured to provide bulk to the splint and to protect the wrist and the forearm of the person covered by the splint; while maintaining a neutral position of the wrist, wrapping a semi-elastic woven stretch material around the second layer of the splint to form a third layer of the splint configured to provide spring and breathability to the splint; and positioning a reinforcement strut on the third layer and securing the reinforcement strut thereto proximate to the wrist such that the reinforcement strut is configured to facilitate maintaining the wrist in a neutral position.

In another aspect, a preferred method of the present invention is for using a custom splint including the steps of: providing a stockinette to the wrist and the forearm, the stockinette being configured to form a first layer of the splint; wrapping a fabric material about the first layer of the splint to form a second layer of the splint configured to provide bulk to the splint and to protect the wrist and the forearm of the person covered by the splint; while maintaining a neutral position of the wrist, wrapping a semi-elastic woven stretch material around the second layer of the splint to form a third layer of the splint configured to provide spring and breathability to the splint; and positioning a reinforcement strut on the third layer and securing the reinforcement strut thereto proximate to the wrist such that the reinforcement strut is configured to facilitate maintaining the wrist in a neutral position.

In another aspect, a preferred method of the present invention is used for manufacturing a custom splint adapted for a person configured for use on a hand, a wrist, and a forearm of the person. The method including the steps of: wrapping a fabric material about a portion of the hand and the forearm of the person to form a second layer of the splint configured to provide bulk to the splint and to protect the wrist and the forearm of the person covered by the splint; while maintaining a neutral position of the wrist, wrapping a semi-elastic woven stretch material around the second layer of the splint to form a third layer of the splint configured to provide spring and breathability to the splint; and positioning a reinforcement strut on the third layer and securing the reinforcement strut thereto proximate to the wrist such that the reinforcement strut is configured to facilitate maintaining the wrist in a neutral position.

In another aspect, the present invention is directed to a custom splint adapted for a person and configured for use on a hand, a wrist, and a forearm of the person. The custom splint includes a stockinette adapted for positioning against the wrist and the forearm, the stockinette being configured to form a first layer of the splint. A fabric material positioned about the first layer of the splint to form a second layer of the splint configured to provide bulk to the splint and adapted to protect the wrist and the forearm of the person covered by the splint. A semi-elastic woven stretch material positioned around the second layer of the splint to form a third layer of the splint configured to provide spring and breathability to the splint. A reinforcement strut positioned on the third layer proximate to the portion of the custom splint adapted to cover the wrist such that the reinforcement strut is configured to facilitate maintaining the wrist in a neutral position.

In another aspect, the present invention is directed to a custom splint adapted for a person and configured for use on a hand, a wrist, and a forearm of the person. The custom splint includes a stockinette adapted for positioning against the wrist and the forearm, the stockinette being configured to form a first layer of the splint. A fabric material positioned about the first layer of the splint to form a second layer of the splint configured to provide bulk to the splint and adapted to protect the wrist and the forearm of the person covered by the splint. A semi-elastic woven stretch material positioned around the second layer of the splint to form a third layer of the splint configured to provide spring and breathability to the splint. A reinforcement strut positioned on the third layer proximate to the portion of the custom splint adapted to cover the wrist such that the reinforcement strut is configured to facilitate maintaining the wrist in a desired position.

In another aspect, a preferred method of the present invention is used for manufacturing a custom splint adapted for a person configured for use on a hand, a wrist, and a forearm of the person. The method including the steps of: wrapping a fabric material about a portion of the hand and the forearm of the person to form a second layer (a first layer may or may not be present in the splint) of the splint configured to provide bulk to the splint and to protect the wrist and the forearm of the person covered by the splint; while maintaining a desired position of the wrist, wrapping a semi-elastic woven stretch material around the second layer of the splint to form a third layer of the splint configured to provide spring and breathability to the splint; and positioning a reinforcement strut on the third layer and securing the reinforcement strut thereto proximate to the wrist such that the reinforcement strut is configured to facilitate maintaining the wrist in the desired position.

In another embodiment the present invention is directed to a splint configured for use on a hand, a wrist, and a forearm of a person including a padding layer. A reinforcement strut is positioned on and/or in the padding layer. The reinforcement strut is configured to deform under use of the hand by the person and then return to a predetermined position once the hand is not in use. A covering layer surrounding the padding layer and the reinforcement strut. The reinforcement may be formed by an elongated polymer comprising a preheated thermoplastic stay. The reinforcement strut may deform from the predetermined position when more than four pounds or more of force is exerted on an end thereof and then may return to the predetermined position when the force is less than four pounds.

In another embodiment the present invention is directed to a splint configured for use on a hand, a wrist, and a forearm of a person including a padding layer. A reinforcement strut is positioned on and/or in the padding layer. The reinforcement strut is configured to deform under use of the hand by the person and then return to a predetermined position once the hand is not in use.

In another embodiment the present invention is directed to a splint configured for use on a hand, a wrist, and a forearm of a person including a padding layer. A reinforcement strut is positioned on and/or in the padding layer. The reinforcement strut is configured to deform under use of the hand by the person and then return to a predetermined position once the hand is not in use. The strut is configured and attached to portions of the splint so that it functions as a leaf spring that is biased toward the predetermined equilibrium position (preferably a neutral wrist position). This results in the strut generating a restorative force whenever the wrist is moved out of the predetermined position. As such the strut can be designed to allow motion while encouraging the wrist back to the normal position. The material of the splint preferably generates heat and massage action due to the allowance of motion of the wrist. The splint may be configured to provide a restorative bias of anywhere between 1-10 pounds of pressure (or any other suitable amount) on the palm and forearm to encourage the wrist back to the predetermined position. Alternatively, the strut can be a two part member connected by a torsion spring to provide the restorative force. Alternatively, the strut can be configured to function as a shock absorber or damper within the splint to allow for motion while slowly encouraging the hand to less motion and back to the predetermined equilibrium position. Similarly, the strut can be configured to provide either one of an increasing or decreasing restorative force as the wrist is moved further out of position.

BRIEF DESCRIPTION OF THE DRAWINGS

The above summary, as well as the following detailed description of the preferred embodiments of the present invention, will be understood when read in conjunction with the appended drawings. For the purpose of illustrating the invention, there are shown in the drawings embodiments which are presently preferred. It is understood, however, that the invention is not limited to the precise arrangement and instrumentalities shown. In the drawings:

FIG. 4 is a cross-sectional view of the custom splint 30 of FIG. 2;

FIG. 5 is a cross-sectional view of the custom splint 30 of FIG. 4 as taken along the lines 5-5 of FIG. 4;

DETAILED DESCRIPTION OF THE PREFERRED EMBODIMENTS

Figure 1:
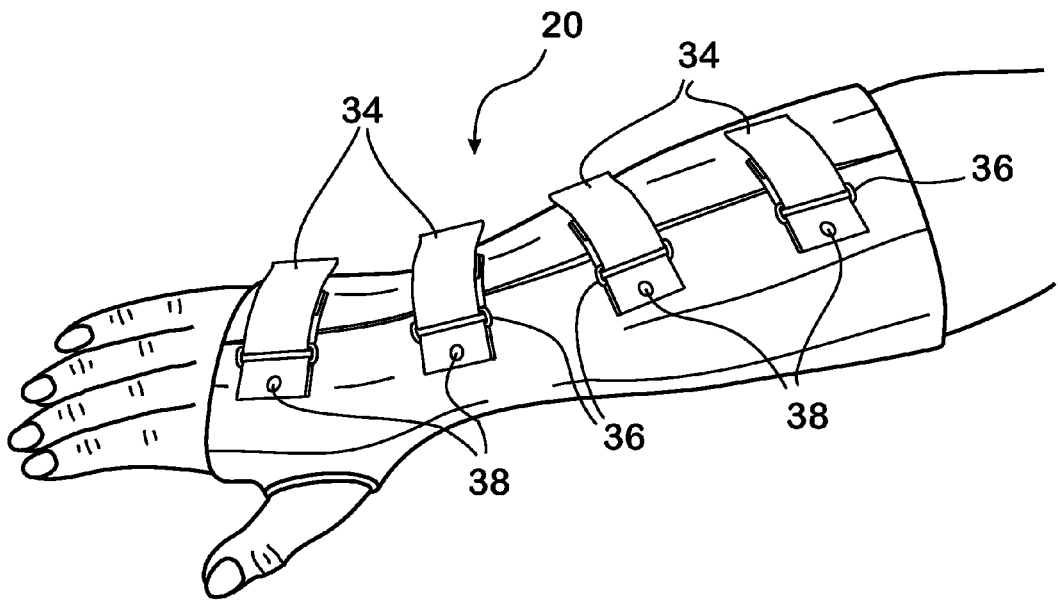
FIG. 1 is a perspective view of a custom splint 30 manufactured according to a preferred method of the present invention; the splint 30 preferably includes a thumb portion 32, Velcro straps 34 that may incorporate D rings 36 and the rivets 38; the splint 30 is shown covering approximately ¾ of a forearm, a wrist, a palm portion of the hand, and the base of a palm of a person.

Certain terminology is used in the following description for convenience only and is not limiting. The word "outer" and/or "outwardly" refer to directions away from or to a location on an outer surface relative to the geometric center of the referenced element and designated parts thereof. The term "splint", as used in the claims and in corresponding portions of the specification, means "a device for isolating an injured portion of a person's body and limiting motion of the injured portion to facilitate healing" and does not include orthopedic devices that are intended to preserve, guide, and correct motion between two different portions of the body to which it is attached. For example, the term "splint" does not include an orthopedic device that attaches to both the upper and lower leg and is configured to guide motion to facilitate normal walking and leg motion while wearing the device due to weakened joints or the like. Additionally, the words "a" and "one" are defined as including one or more of the referenced item unless specifically stated otherwise. The terminology includes the words above specifically mentioned, derivatives thereof, and words of similar import.

Briefly speaking, the splints 30 of the present invention are preferably made of various materials. Those of ordinary skill in the art will appreciate that any suitable splint material can be used without departing from the scope of the present invention. The splint of the present invention is a specific splint 30 which preferably gives support, proper neutral positioning of the wrist and which allows freedom of motion for activities.

This splint 30 is preferably formed as a tape wrist splint and is unique and something that actually facilitates recovery in most people. Experimental data has shown that about fifty percent (50%) of carpal tunnel disorders as well as an even greater percentage of hand and wrist tendinitis; respond to the splints of the present invention, conservative care, and are cured without surgery. This is the literature and the experience of this inventor and hand surgeon. This splint can be used to treat tendinitis at the wrist and forearm and elbow. Arthritis, synovitis, basal joint arthritis, fractures, Tennis Elbow, forearm pain and wrist and hand pain are all treatable easily and consistently using the splint of the present invention.

Some Preferred Features Of The Splint Of The Present Invention may include semi-elastic material
    preferably holds the wrist in a neutral position
    may use an orthoplastic, suitable polymer, or semi-rigid zero degree piece
    preferably, but not necessarily, not a cock up type splint
    preferably allows protected motion with support
    preferably physiologic allowing muscle development and prevents atrophy
    preferably prevents abnormal and overuse syndromes
    preferably calms tendinitis and nerve irritability
    conformable and comfortable
    preferably includes adjustable straps for various degrees of tightness
    preferably allows protected motion with its semi-flexible hinge support strut 58 (also referred to as reinforcement strut 58) yet excellent stability
    preferably a neutral functional protective and healing device
    preferably the outer portion and materials may be layered wrapped in formation of the splint Preferably wearing the splint 30 of the present invention allows protected motion and a calming effect on the flexor tendons and the median nerve which traverse the carpal tunnel and travel through the forearm to the hand and fingers. Unlike conventional rigid and awkwardly positioned splints, the tape splint 30 offers the advantage of actually soothing and massaging the soft tissues through its unique protective design, adding heat as well as a massaging of the tissues through compression with any motion of the hand, wrist and digits, almost by its very nature calming tenosynovitis and inflammation of the structures (epineurium) surrounding the median nerve at the carpal canal. The importance of wrist position in healing is significant. In cases of carpal tunnel and tendinitis, the literature clearly shows with manometric intracarpal catheters and ultrasound examinations that posturing of the wrist in flexion or extension puts more pressure on the median nerve and tendon structures. Therefore the splint of present invention, which preferably, but not necessarily, encourages posturing of the wrist in neutral, in contradistinction to other "cock up splints", is superior and unique in its ability to treat carpal tunnel injury. Additionally, the splint's 30 heat and massage action generated by the action of the layers and reinforcement strut during use of the hand provides superior treatment of carpal tunnel injury.

The Pathophysiology Of Carpal Tunnel And Tendinitis

Repeated stress and strain on the flexor tendons results in chronic inflammatory change and ultimately compression of the median nerve at the carpal canal. Other associated issues resulting from this tendinitis and the involvement over time of the synovium surrounding the flexor tendons and at times the extensor mechanism and forearm as well. There is no clear answer as to when conservative treatment will not work in that it is difficult to ascertain how much of the symptom production is from the inflammatory issue, which does respond to conservative treatment very nicely, and how much from well formed scar about the nerve and tendon structures which is the ultimate cause of irreversible disease.

The neuro pathophysiology of the development of this disease is that eventually the surrounding tissue of the nerve becomes scarred and once this scar tissue becomes fixed we have developed a permanent long-term nerve injury. This results in ongoing numbness and tingling and nerve symptoms and ultimately positive EMG nerve conduction studies.

As this progresses function deteriorates and the cumulative traumas increase and progress each day that is worked or the hand is used in a manner which stresses this mechanism. Once we have permanent scarring and a nerve this becomes an irreversible process and we have permanent nerve injury. Although we may be able to calm down the symptoms there will be ongoing dysfunction which is variable in degree with each patient. Even with surgical intervention, 30% of patients continue to have symptoms or have recurrent problems. These numbers are even worse if the patient is sent back to the same said activities which caused the problem in the first place. This makes it reasonable to attempt conservative care first and see how much of the process is from reversible inflammation and how much from permanent scarring. In our experience up to 50% of patients respond, at least in part, to conservative care.

Referring to FIG. 1 a custom splint 30 can be manufactured according to a preferred method of the present invention. However, the present invention includes splints of similar construction regardless of how manufactured. The steps in one method of manufacturing the splint will be described below in conjunction with the discussion of the drawings.

Figure 2:
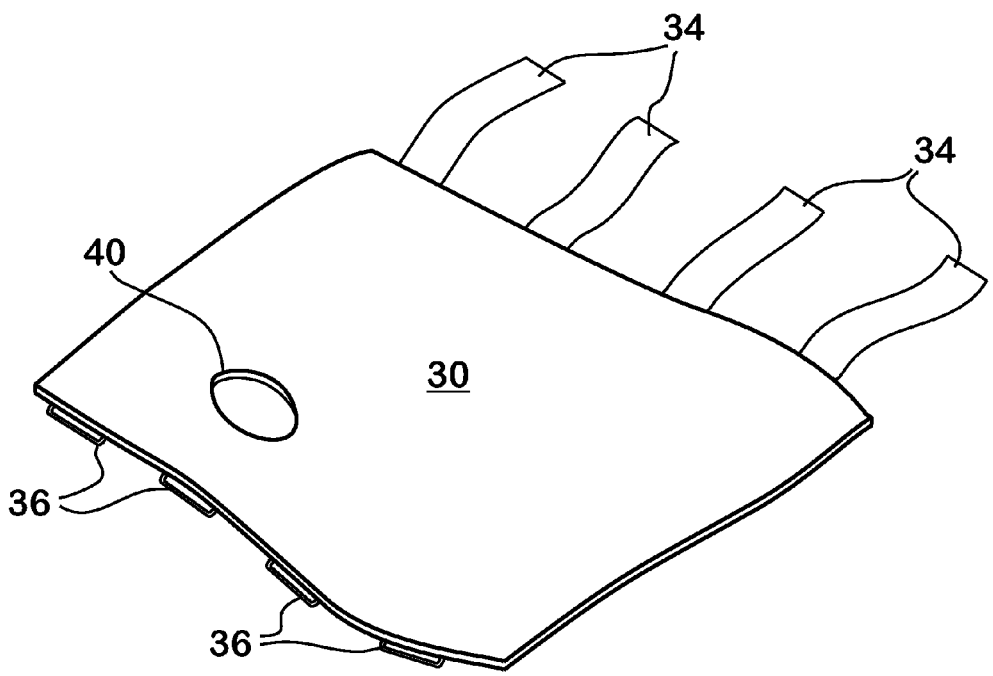
FIG. 2 is a perspective view of the splint 30 of FIG. 1 not worn by a person; a thumb hole 40 is clearly visible in this view.
Figure 3:
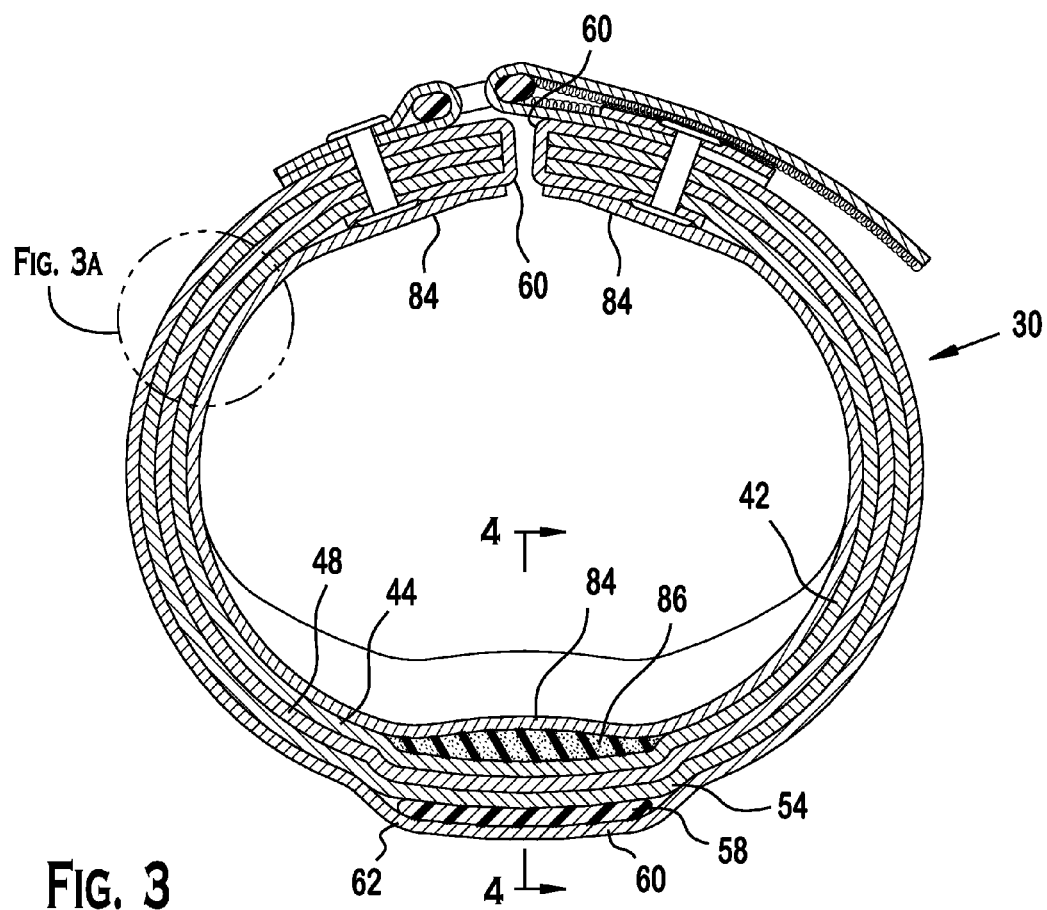
FIG. 3 is a cross-sectional view of the custom splint 30 of FIG. 1.
Figure 3A:
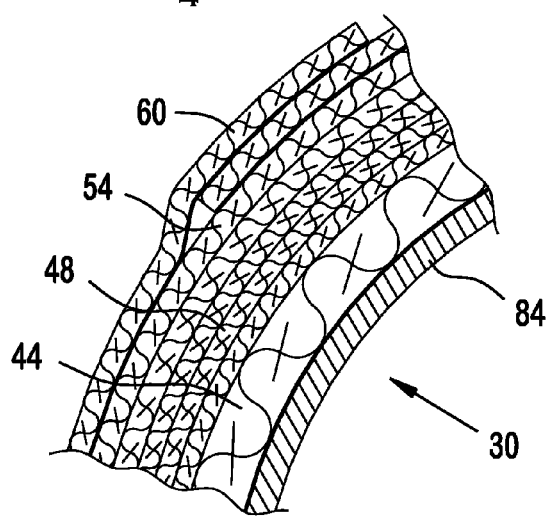
FIG. 3A is an enlarged, partial, broken away of the custom splint 30 of FIG. 3.
Figure 6:
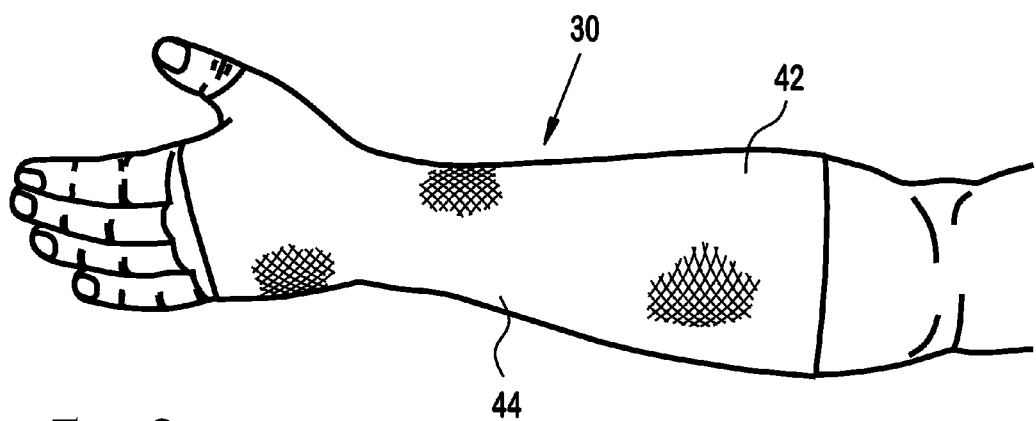
FIG. 6 is a perspective view of a person's arm positioned comfortably with a stockinette 42 applied thereto over the wrist and the forearm; the stockinette/sock 42 is preferably configured to form a first layer 44 of the splint 30; this stockinette 42 is preferably configured to cover at least three fourths of the forearm of the person; the sock may include a thumb portion.

The splint 30 preferably includes a thumb portion 32, Velcro straps 34 that may incorporate D rings 36, and rivets 38. The splint 30 may cover approximately ¾ of a forearm, a wrist, a palm portion of the hand, and the base of a palm of a person. Referring to FIG. 2, the splint 30 of FIG. 1 is shown when not worn by a person. A thumb hole 40 may be incorporated in the splint 30. Referring to FIG. 6, a person's arm is positioned comfortably with a stockinette 42 (also referred to as a sock) applied thereto over the wrist and the forearm. While it is preferred that the splint 30 of the present invention include a sock 42, those of ordinary skill in the art will appreciate from this disclosure that the sock 42 can be eliminated without departing from the scope of the present invention. The stockinette/sock 42 is preferably configured to form a first layer 44 of the splint 30. The stockinette 42 is preferably configured to cover at least three fourths of the forearm of the person. The sock 42 may include a thumb portion.

Figure 7:
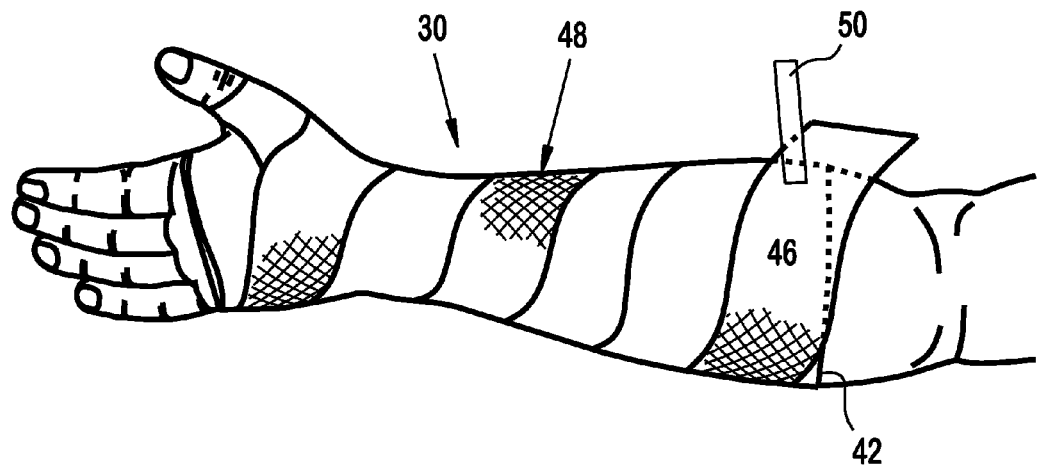
FIG. 7 is a perspective view illustrating a fabric material 46 wrapped about the first layer 44 of the splint 30 to form a second layer 48 of the splint 30 which is preferably configured to provide bulk to the splint and to protect the wrist and forearm of the person wearing the splint 30; the fabric material 46 is preferably, but not necessarily, a cotton cling material, the cotton cling material may be wrapped web roll that can be used to add bulk, warmth, and protection to a person wearing the splint 30; it is preferable that the fabric material 46 is secured using tape 50; one suitable fabric material 46 could be Artiflex cling.

Referring to FIG. 7, a fabric material 46 is preferably wrapped about the first layer 44 of the splint 30 to form a second layer 48 of the splint 30 which is preferably configured to provide bulk to the splint and to protect the wrist in form of the person covered by the splint 30. The fabric material 46 is preferably, but not necessarily, a cotton cling material. The cotton cling material may be wrapped web roll that can be used to add bulk, warmth, and protection to a person wearing the splint 30. It is preferable that the fabric material 46 is secured using tape 50. One suitable fabric material 46 that can be used is Artiflex cling. However, one of ordinary skill in the art will appreciate from this disclosure that any suitable fabric material can be used without departing from the scope of the present invention.

Figure 8:
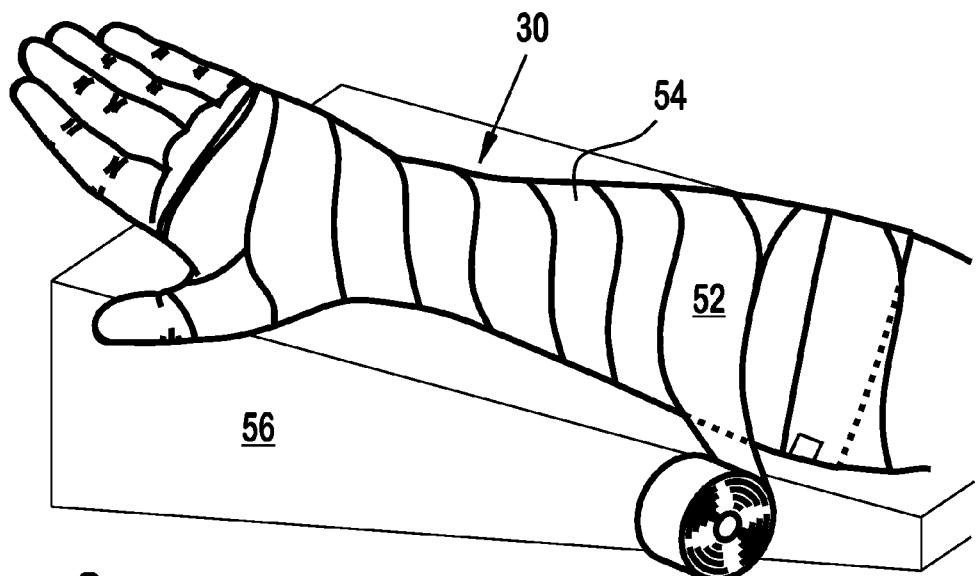
FIG. 8 is a perspective view illustrating a semi-elastic woven stretch material 52 being wrapped around the second layer 48 of the splint 30 to form a third layer 54; the third layer 54 is preferably configured to provide spring and breathability to the splint 30; it is preferable, but not necessary, that the extremity is supported by a support 56 during the wrapping to facilitate maintaining the wrist in a neutral position during wrapping; those of ordinary skill in the art will appreciate that the wrist can be maintained in a position other than neutral without departing from the scope of the present invention; the semi-elastic stretch material that forms the third layer 54 preferably provides spring and breathability to the custom splint 30; the layer of semi-elastic material preferably further provides room in the splint for compression and relaxation thereof which helps to provide massage action during normal use; it is preferable that there are three layers of semi-elastic material; however, those of ordinary skill in the art will appreciate that any number of semi-elastic material 52 layers can be used without departing from the scope of the present invention; one suitable semi-elastic stretch material 52 could be 2 inch Coban; Either neoprene, Artiflex, or any other suitable material can be used to form one of the layers of the custom splint 30.

As shown in FIG. 8, a semi-elastic woven stretch material 52 may be wrapped around the second layer 48 of the splint 30 to form a third layer 54. The third layer 54 is preferably configured to provide spring and breathability to the splint 30. It is preferable, but not necessary, that the extremity (person's forearm and hand) is supported by a support 56 during the wrapping to facilitate maintaining the wrist in a neutral position during wrapping. Those of ordinary skill in the art will appreciate that the wrist can be maintained in a position other than neutral without departing from the scope of the present invention. The semi-elastic stretch material that forms the third layer 54 preferably provides spring and breathability to the custom splint 30. The layer of semi-elastic material preferably further provides room in the splint for compression and relaxation thereof which helps to provide massage action during normal use. It is preferable that there are three layers of semi-elastic material used to form the third layer 54. However, those of ordinary skill in the art will appreciate that any number of semi-elastic material 52 layers can be used without departing from the scope of the present invention. One suitable semi-elastic stretch material 52 would be 2 inch Coban.

Figure 9:
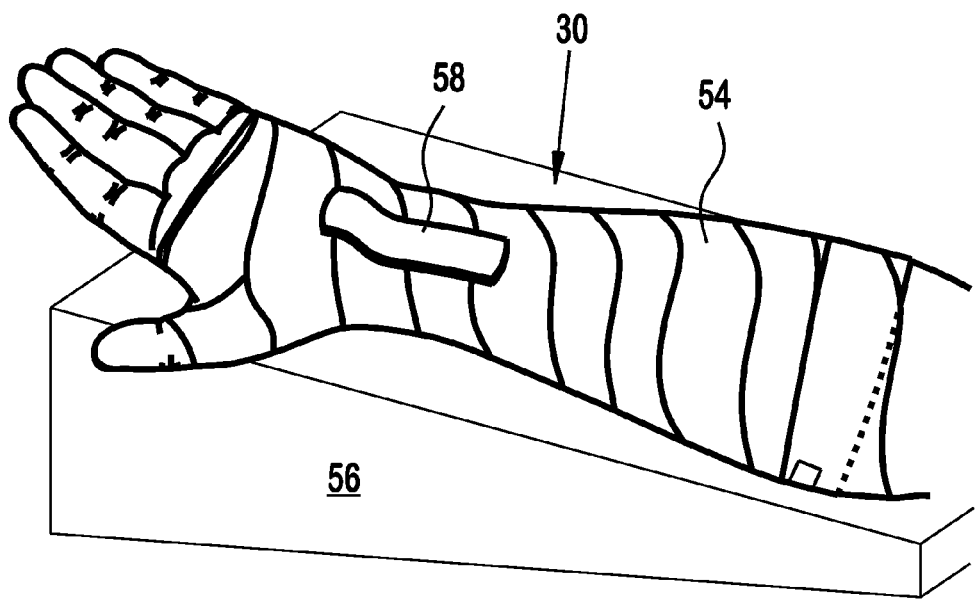
FIG. 9 is a perspective view illustrating the positioning of a reinforcement strut 58 on the third layer 54 of the splint 30 for securing thereto proximate to the wrist such that the reinforcement strut 58 is configured to facilitate maintaining the wrist in a desired position (such as, the neutral position); it is preferred that the reinforcement strut 58 is formed by an elongated polymer member that may be generally aligned parallel to a longitudinal axis of the custom splint 30; it is also preferred, but not necessary, that the reinforcement strut 58 is positioned/configured to extend over the wrist area to facilitate maintaining the wrist in a desired position when the custom splint 30 is worn; the reinforcement strut 58 is preferably formed by a preheated thermoplastic stay and may have a length of between 2 inches and 5 inches and the width of between a quarter of an inch and 2 inches. It is more preferable still that the elongated polymer have a length of between 3 inches and 4 inches and a width of between three quarters of an inch and one half of an inch; it is more preferable still that the elongated polymer reinforcement strut 58 have a length of between 3 inches and 4 inches and the width of between three quarters of an inch and 1½ inches. However, those of ordinary skill in the art will appreciate from this disclosure that the dimensions of the reinforcement strut 58 can be varied without departing from the scope of the present invention; For example, the length of the strut could be approximately nine inches and the width approximately four inches without departing from the present invention; the reinforcement strut 58 may provide semi-rigidity to the splint 30 by preferably using a heatable/moldable polymer at just about the wrist area; this preferably provides a little more rigidity to the splint 30 and keeps the wrist in the desired position.

Referring to FIG. 9, a reinforcement strut 58 on the third layer 54 of the splint 30 for securing thereto proximate to the wrist such that the reinforcement strut 58 is configured to facilitate maintaining the wrist in a desired position (such as, the neutral position). It is preferred that the reinforcement strut 58 is formed by an elongated polymer member that may be generally aligned parallel to a longitudinal axis of the custom splint 30. It is also preferred, but not necessary, that the reinforcement strut 58 is positioned/configured to extend over the wrist area to facilitate maintaining the wrist in a desired position when the custom splint 30 is worn. The reinforcement strut 58 is preferably formed by a preheated thermoplastic stay and may have a length of between 2 inches and 5 inches and the width of between a quarter of an inch and 2 inches. It is more preferable still that the elongated polymer have a length of between 3 inches and 4 inches and a width of between three quarters of an inch and one and a half inches. It is more preferable still that the elongated polymer reinforcement strut 58 have a length of between 3 inches and 4 inches and the width of between three quarters of an inch and 1½ inches. However, those of ordinary skill in the art will appreciate from this disclosure that the dimensions of the reinforcement strut 58 can be varied without departing from the scope of the present invention. The reinforcement strut 58 provides semi-rigidity to the splint 30 by preferably using a heatable/moldable polymer at just about the wrist area. This preferably provides a more rigidity to the splint 30 and keeps the wrist in the desired position. The orthoplast length could be up to 9 inches and the width up to 4 inches for (or any other suitable length) more secure support of the forearm and wrist as indicated.

Figure 10:
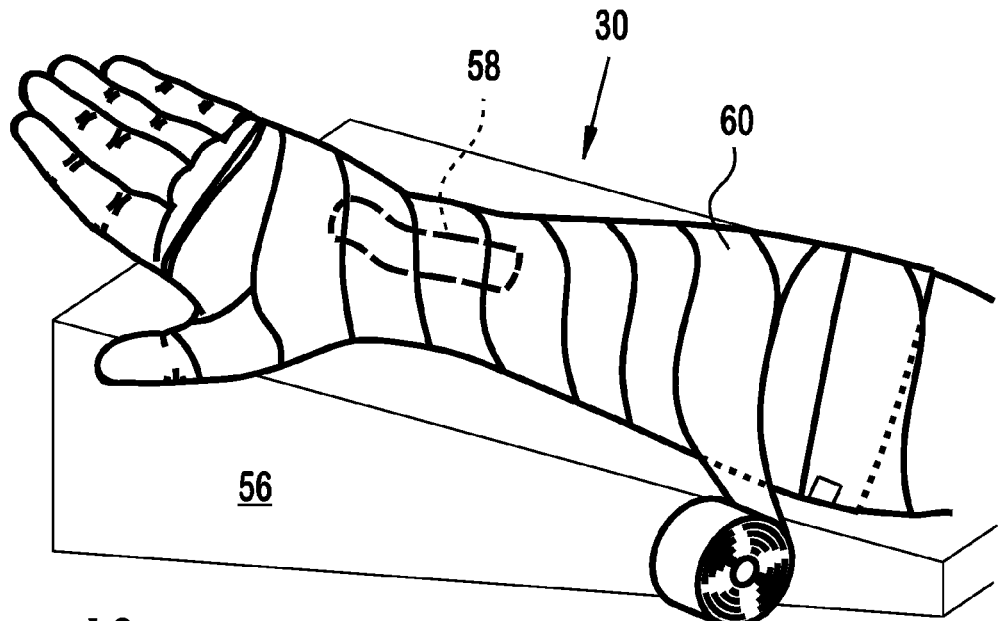
FIG. 10 is a perspective view of the splint 30 with semi-elastic tape 60 being wrapped over the reinforcement strut 58 and the third layer 54 of the splint 30 to secure the position of the reinforcement strut 58 within the splint 30 and to form a fourth layer 62 of the splint 30 configured to provide additional support for the forearm and hand; the semi-elastic tape is preferably a porous, elastic tape 60; one suitable type of such tape would be Tensoplast tape; the semi-elastic, porous tape provides additional bulk and support for the forearm and hand; it is preferable that two layers of semi-elastic tape 60 are formed as the fourth layer of the splint 30; however, those of ordinary skill in the art will appreciate from this disclosure that any number of layers of semi-elastic, porous tape can be used without departing from the scope of the present invention; it is preferable, but not necessary, that when wrapping the first layer, the second layer, the third layer, and the fourth layer of the custom splint 30 that the layers are positioned to cover at least a portion of the thumb; While in one preferred embodiment of the splint 30, the splint is made by wrapping it about a person's arm, those of ordinary skill in the art will appreciate that the splint of the present invention can be manufactured using any suitable process including having layers of material attached together as part of an automated process in which predetermined and/or standard dimensions are used for the splints.

As shown in FIG. 10, semi-elastic tape 60 is preferably wrapped over the reinforcement strut 58 and the third layer 54 of the splint 30 to secure the position of the reinforcement strut 58 within the splint 30 and to form a fourth layer 62 of the splint 30 configured to provide additional support for the forearm and hand. The semi-elastic tape is preferably a porous, elastic tape 60. One suitable type of such tape would be Tensoplast tape. The semi-elastic, porous tape provides additional bulk of support for the forearm and hand. It is preferable that two layers of semi-elastic tape 60 are formed as the fourth layer of the splint 30. However, those of ordinary skill in the art will appreciate from this disclosure that any number of layers of semi-elastic, porous tape can be used without departing from the scope of the present invention. It is preferable, but not necessary, that when wrapping the first layer, the second layer, the third layer, and the fourth layer of the custom splint 30 that the layers are positioned to cover at least a portion of the thumb. The outer layer may be of another material and method of creation such as Neoprene and is not wrapped around the individuals arm in the formation but surrounds the inner materials. For example the splint can be formed by layering or some other automated process.

Figure 11:
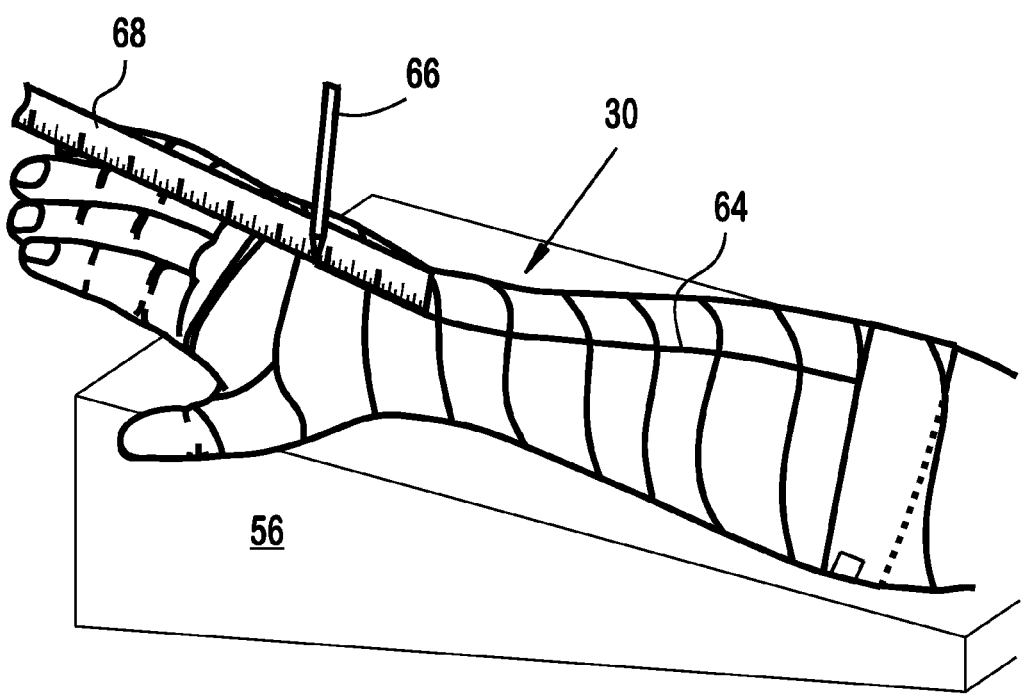
FIG. 11 is a perspective view of the splint 30 with the person's wrist in a prone position (i.e., preferably with the palm facing downwards) on the supporting surface 56 to allow a cut to be made on the back of the splint 30 to allow the splint to be removed and positioned on the wearer; a path 64 is preferably marked along an outer surface of the custom splint 30 from approximately the third metatarsophalangeal (MCP) joint drawing a line generally down the middle of the splint 30; this is preferably done using a grease pen 66 and a ruler 68 to draw a generally straight line from the third MCP joint down the middle of the splint.
Figure 12:
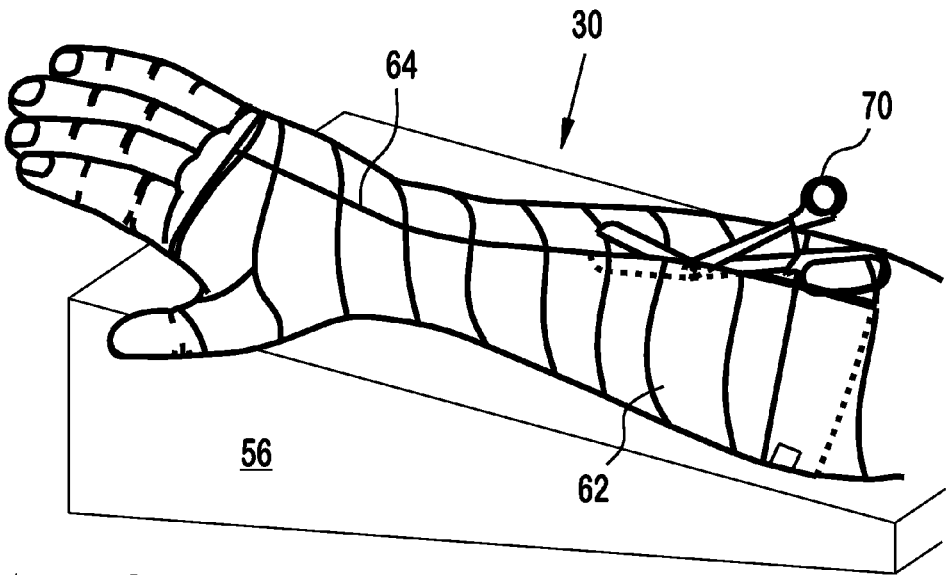
FIG. 12 is a perspective view of the splint 30 of the present invention showing the cutting along the path 64 to cut along a preferably straight line from the third MCP joint down the middle of the splint 30; the cutting may be performed using appropriate scissors 70 or any other suitable instrument without departing from the scope of the present invention.
Figure 13:
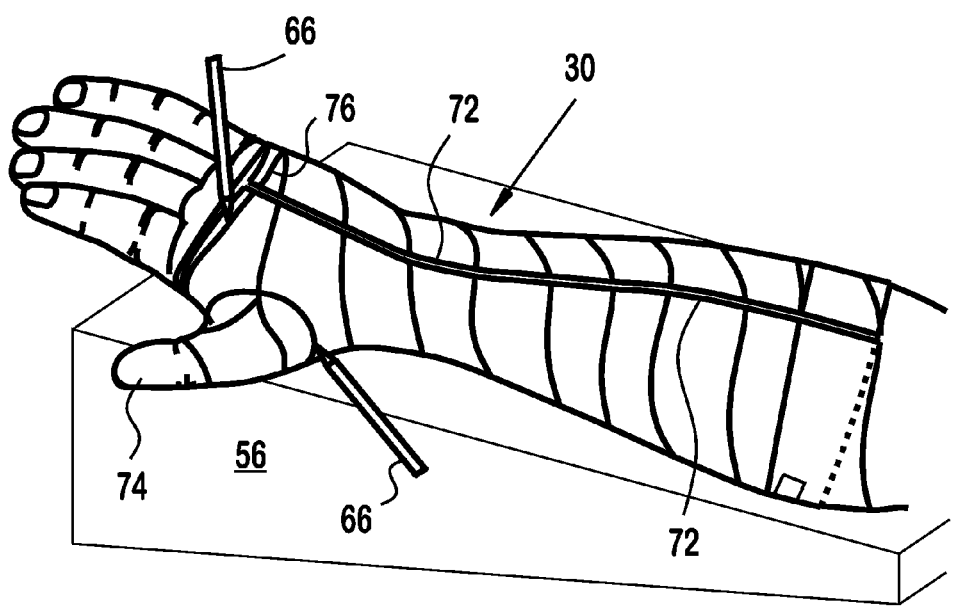
FIG. 13 illustrates the splint 30 of the present invention after the cut has been made along path 64; the cutting of the path 64 results in two vertical edges 72 being formed in the splint 30; areas around the thumb 74 and the transverse palmar crease 76 are preferably marked.

Referring to FIG. 11, a person's wrist is preferably aligned in a prone position (i.e., preferably with the palm facing downwards) on a supporting surface 56 to allow a cut to be made on the back of the splint 30 to allow the splint to be removed and positioned on the wearer. A path 64 is preferably marked along an outer surface of the custom splint 30 from approximately the third metatarsophalangeal (MCP) joint and drawing a line down the middle of the splint 30. This is preferably done using a greased pen 66 (or any other suitable writing instrument) and a ruler 68 to draw a straight line from the third MCP joint down the middle of the splint 30. Referring to FIG. 12, scissors or any other suitable tool can be used to cut along the path 64 from the third MCP joint down the middle of the splint 30. As shown in FIG. 13, the cutting of the path 64 results in two vertical edges 72 being formed in the splint 30; areas around the thumb 74 and the transverse palmar crease 76 are preferably then marked.

Figure 14:
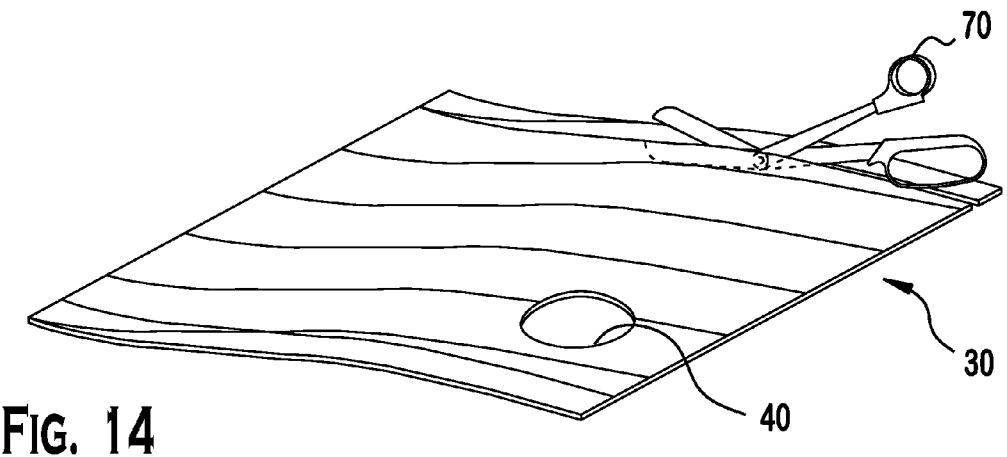
FIG. 14 illustrates the next step in manufacturing the splint 30 of the present invention and shows the splint 30 removed from the person's hand as shown in FIG. 13; the splint is cut along lines that were marked in FIG. 13.
Figure 15:
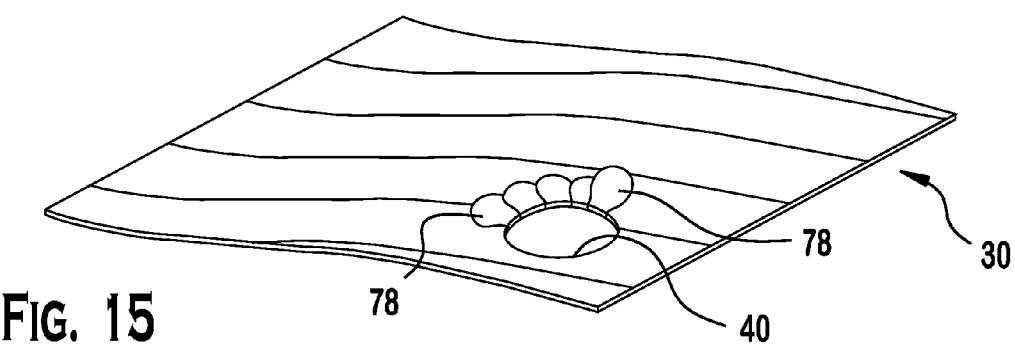
FIG. 15 illustrates the next step in manufacturing the splint 30 which preferably includes positioning soft woven fabric petals with a pile texture thereon 78 on one side along the thumb hole 40 in the custom splint 30 to protect the wearer against abrasion.
Figure 16:
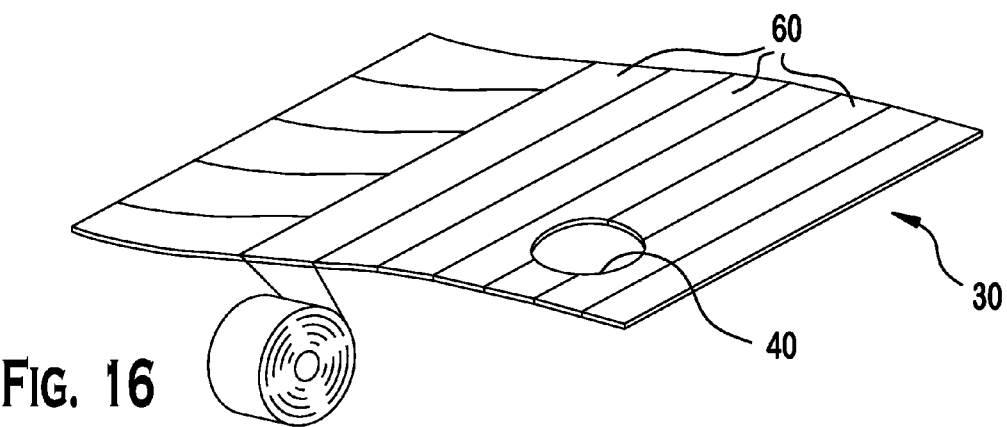
FIG. 16 illustrates strips of porous elastic tape 60 along an inner surface of the custom splint proximate to the area of the reinforcement strut 58 to attempt reduce abrasion during use of the custom splint 30; additionally, strips of the porous elastic tape 60 may be wrapped around the two vertical edges of the custom splint 30; the folded tape strips are preferably aligned along a longitudinal axis of the splint 30; the covering of the vertical edges 72 preferably creates smooth edges proximate the opening of the custom splint 30.

As shown in FIG. 14, the next step in manufacturing the splint 30 of the present invention is to remove the splint from the person's hand and cut along lines that were marked. Referring to FIG. 15, soft woven fabric petals with a pile texture thereon 78 may be positioned on one side along the thumb hole 40 in the custom splint 30 to protect the wearer against abrasion. Strips of porous elastic tape 60 may be positioned along an inner surface of the custom splint proximate to the area of the reinforcement strut 58 to attempt reduce abrasion during use of the custom splint 30 as shown in FIG. 16.

Strips of the porous elastic tape 60 may be wrapped around the two vertical edges of the custom splint 30. The folded strips are preferably aligned along a longitudinal axis of the splint 30 to cover the vertical edges 72 and preferably create smooth edges proximate the opening of the custom splint 30.

Figure 17:
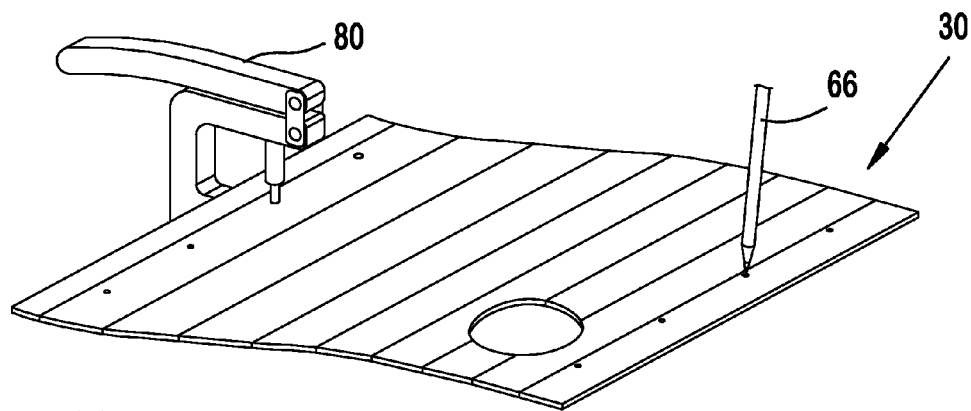
FIG. 17 illustrates the use of a greased pen to mark where rivets and straps will be placed; it is preferable that the splint have four Velcro straps that are generally equally spaced apart by approximately 1 to 1½ inches; however, those of ordinary skill in the art will appreciate from this disclosure that any number or positioning of straps and rivets may be used without departing from the scope of the present invention; hole punch 80 may be used to punch holes on both sides of the splint 30.
Figure 18:
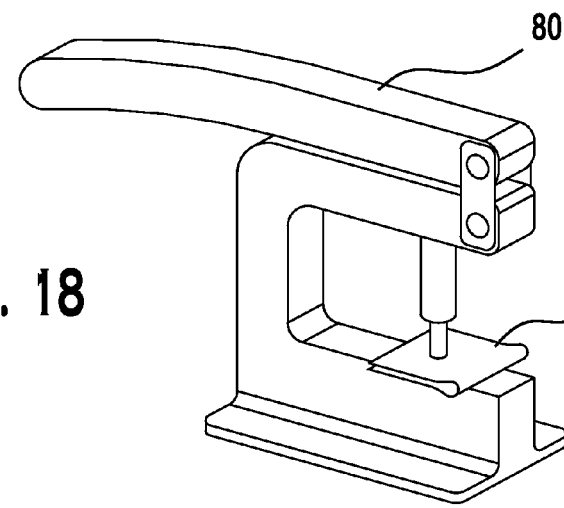
FIG. 18 illustrates the use of the hole punch 80 to form a hole in both ends of a Velcro strap 34.
Figure 19:
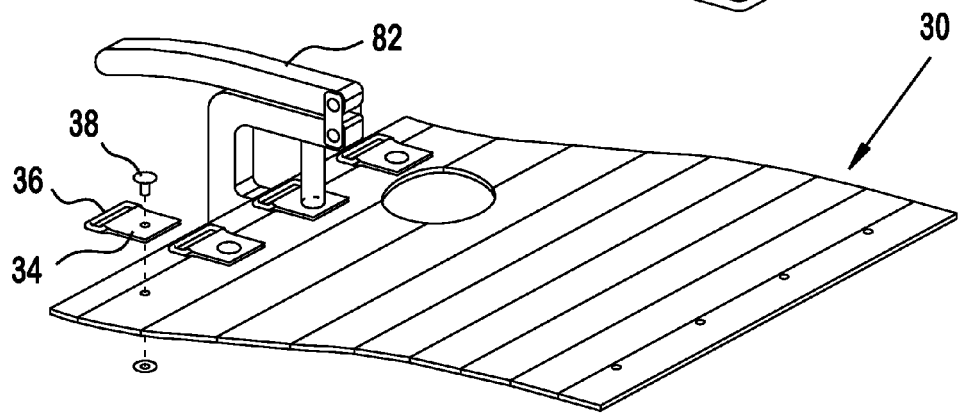
FIG. 19 illustrates the attachment of part of the Velcro straps to the splint 30; the Velcro strap 34 shown in FIG. 18 preferably has a D ring 36 inserted therein after the holes are created; then, with the strap 34 folded through the D ring 36, a rivet 38 is placed through the free ends of the Velcro strap 34 and the splint 30 to secure the Velcro strap 34 to the splint 30.
Figure 20:
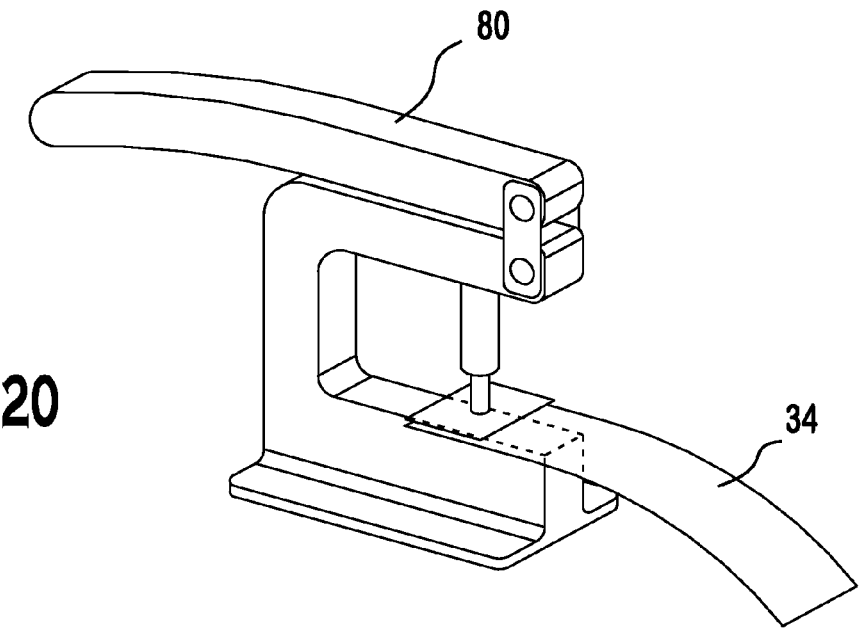
FIG. 20 shows the hole punch 80 used to form holes in one portion of the other half of the Velcro straps 34.
Figure 21:
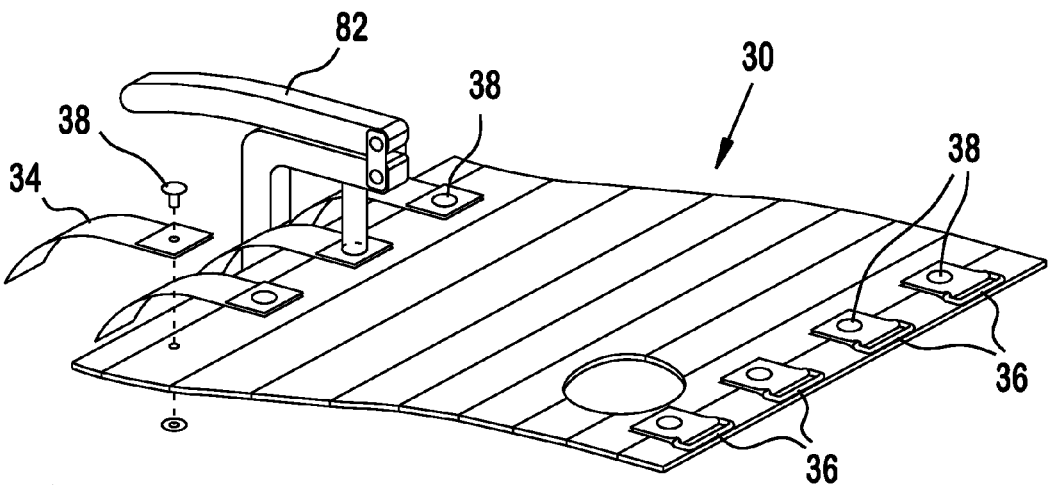
FIG. 21 illustrates a press 82 used to secure the half of the Velcro straps 34 shown in FIG. 2 to the splint 30 using rivets 38.

Referring to FIG. 17, a grease pen may be used to mark where rivets and straps will be placed. It is preferable that the splint have four Velcro straps that are generally equally spaced apart by approximately 1 to 1½ inches. However, those of ordinary skill in the art will appreciate from this disclosure that any number or positioning of straps and rivets may be used without departing from the scope of the present invention. Hole punch 80 may be used to punch holes on both sides of the splint 30. As shown in FIG. 18, the hole punch 80 cam be used to form a hole in both ends of a Velcro strap 34. Referring to FIG. 19, attachment of part of the Velcro straps to the splint 30 preferably includes a D ring 36 inserted therein after the holes are created. Then, with the strap 34 folded through the D ring 36, a rivet 38 is placed through the free ends of the Velcro strap 34 and the splint 30 to secure the portion of the Velcro strap 34 to the splint 30. As shown in FIG. 20, the hole punch 80 may then be used to form holes in portions of the other half of the Velcro straps 34. Referring to FIG. 21, a press 82 may be used to secure the half of the Velcro straps 34 using rivets 38.

Figure 22:
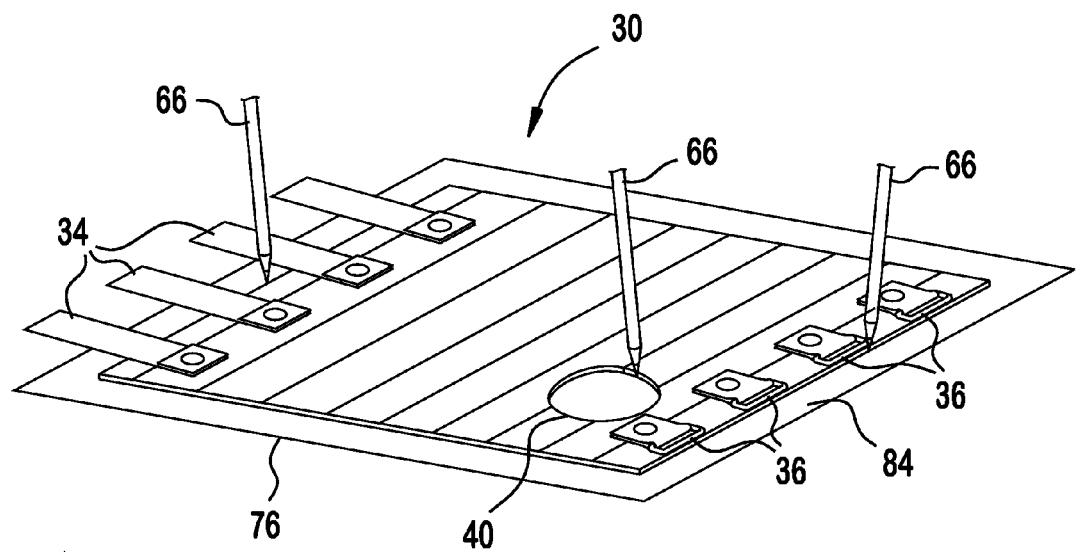
FIG. 22 illustrates a sheet 84 of soft woven fabric with tiled texture on one side 78 positioned below the splint 30; it is preferable that a grease pen 66 is used to trace the outline of the splint on to the sheet and mark the inside perimeter of the thumb opening 40; it is advisable to take care in maintaining the splint 30 in a flat orientation on the sheet 84.

Referring to FIG. 22, a sheet 84 of soft woven fabric with tiled texture on one side 78 is preferably positioned below the splint 30. A grease pen 66 can be used to trace the outline of the splint 30 onto the sheet 84 and mark the inside perimeter of the thumb opening 40. It is advisable to take care in maintaining the splint 30 in a flat orientation on the sheet 84.

Figure 23:
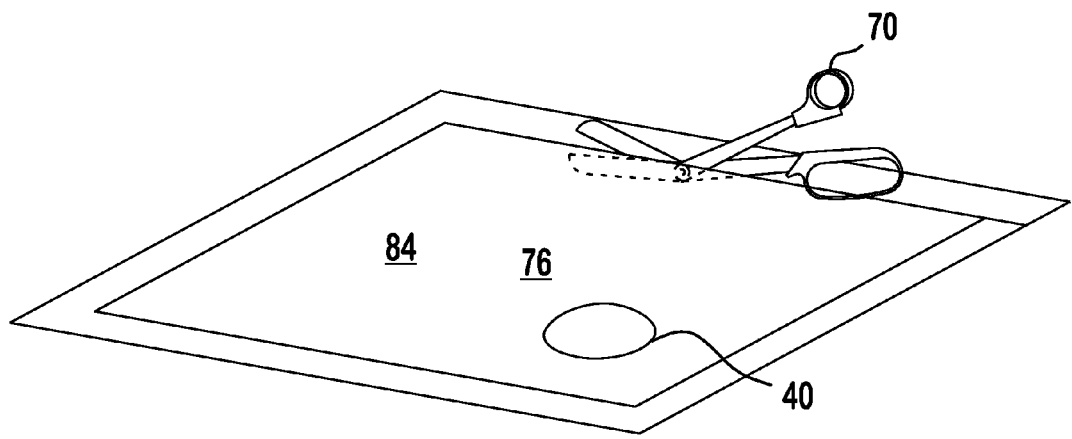
FIG. 23 is a perspective view illustrating scissors 70 cutting the sheet 84 along the markings made in FIG. 22.
Figure 24:
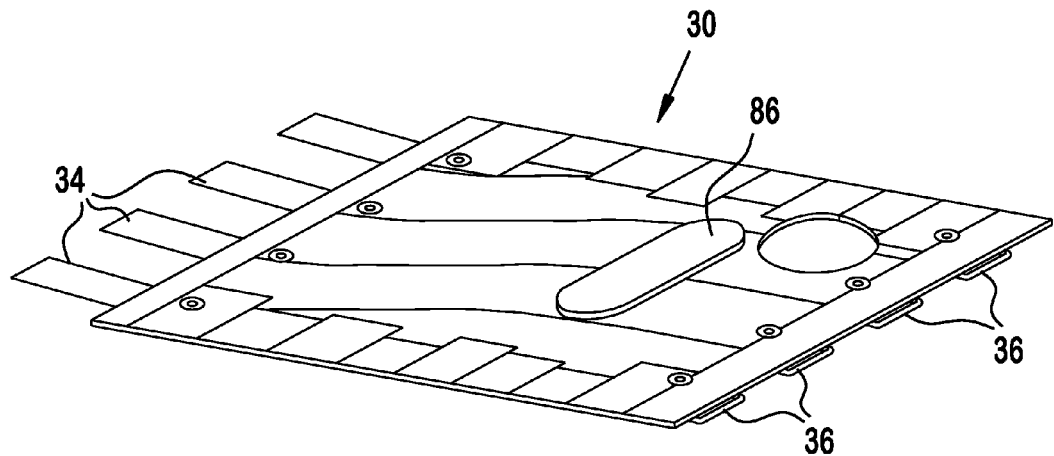
FIG. 24 illustrates the placement of a foam pad 86 along an inner surface of the inner surface of the splint 30 to provide cushioning proximate the reinforcement strut 58.
Figure 25:
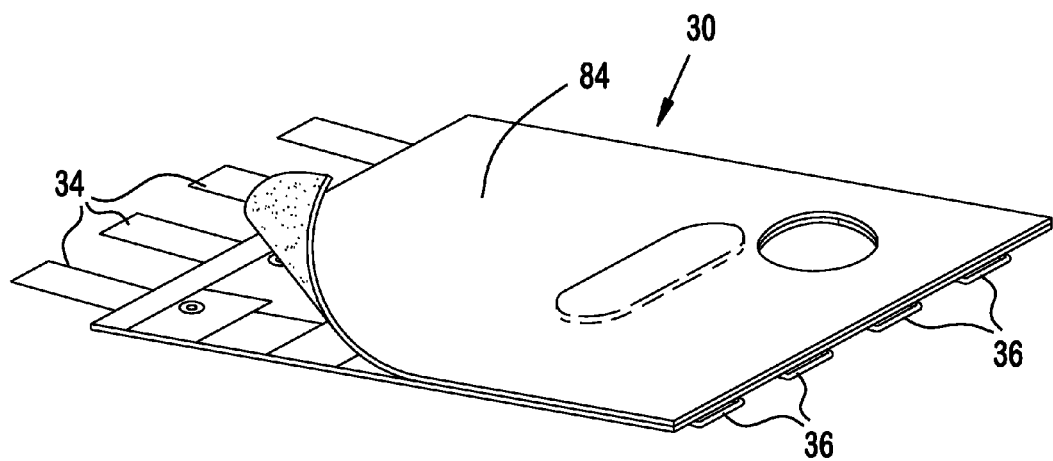
FIG. 25 illustrates placement of the sheet 84 positioned over the inner surface of the splint 36; this preferably increases the comfort and wearability of the splint 30; alternatively, the outer surfaces of the splint 30 may be covered in neoprene without departing from the scope of the present invention; one of ordinary skill in the art will appreciate from this disclosure that Tenoplast tape may or any suitable material may be substituted for another material such as Neoprene and the splint may be cut and shaped without wrapping and the outer layer would consist of a semiporous material like Neoprene and this would support and contain the inner layers replacing the tape and wrapping semielastic outer layers.

As shown in FIG. 23, scissors 70 may be sued to cut the sheet 84 along the markings Referring to FIG. 24, a foam pad 86 can be placed along an inner surface of the splint 30 to provide cushioning proximate the reinforcement strut 58. Referring to FIG. 25, the sheet 84 may be positioned over the inner surface of the splint 36 and secured thereto to preferably increase the comfort and wearability of the splint 30. Alternatively, the outer surfaces of the splint 30 may be covered in neoprene without departing from the scope of the present invention.

Figure 26:
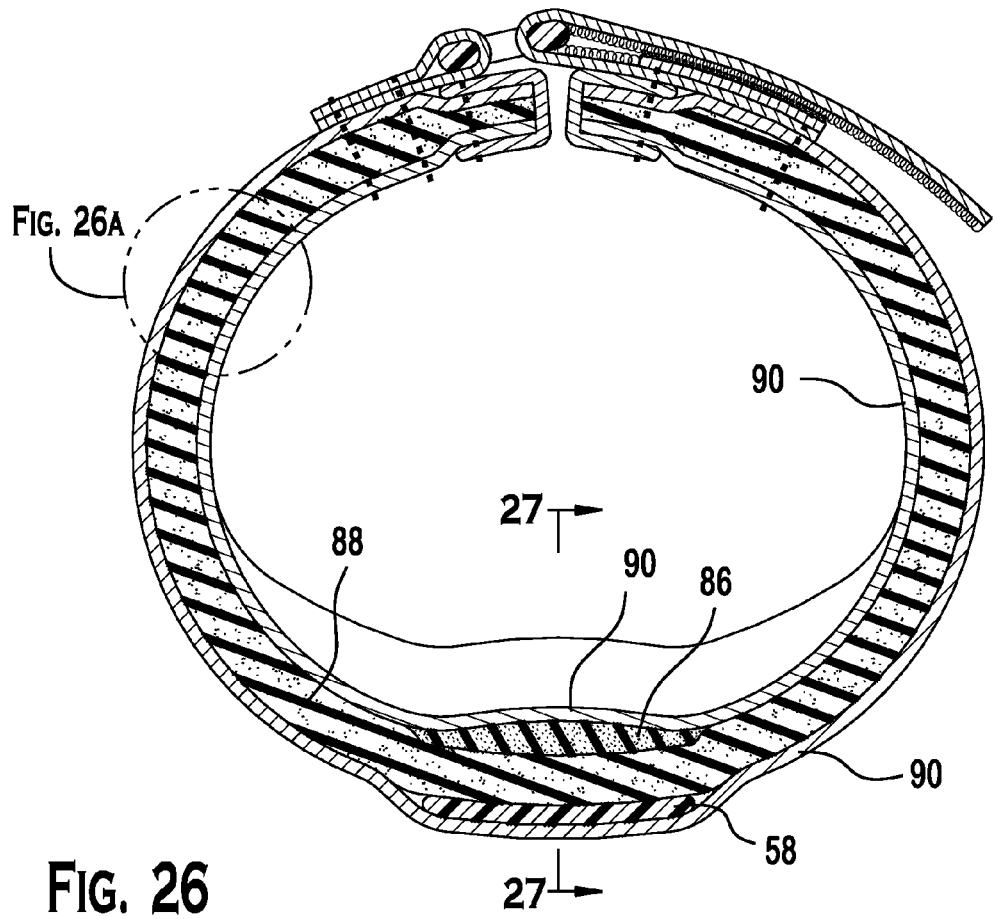
FIG. 26 illustrates a second embodiment of the splint 30 of the present invention in which a single cushioning layer 88 is used with the reinforcement strut 58 placed thereon and the foam pad 86 placed on an opposite side of the splint 30; it is preferable that the splint is wrapped in neoprene 90.
Figure 26A:
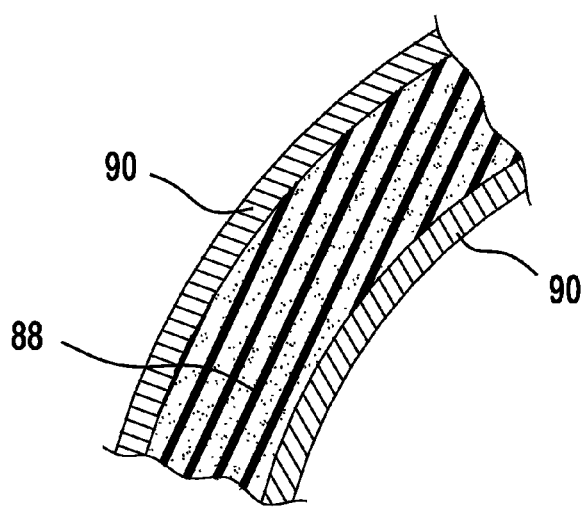
FIG. 26A is a partial, enlarged, broken away view of the splint 30 of FIG. 26 as shown by the phantom circle in FIG. 26.
Figure 27:
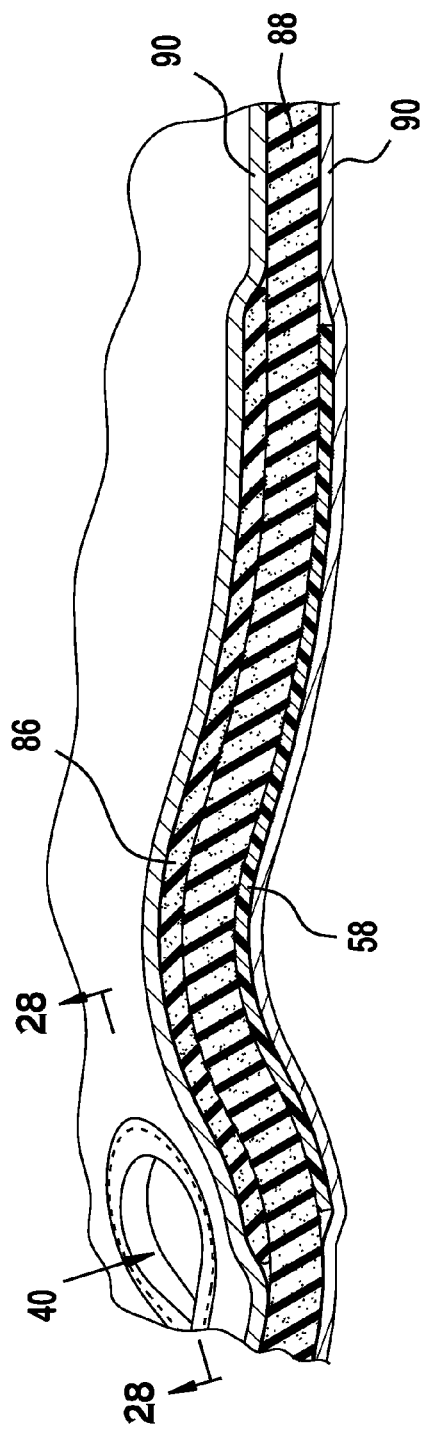
FIG. 27 illustrates cross-sectional views of the splint of FIG. 26; one of ordinary skill in the art will appreciate from this disclosure that Tenoplast tape may or any suitable material may be substituted for another material such as Neoprene and the splint may be cut and shaped without wrapping and the outer layer would consist of a semiporous material like Neoprene and this would support and contain the inner layers replacing the tape and wrapping semielastic outer layers
Figure 28:
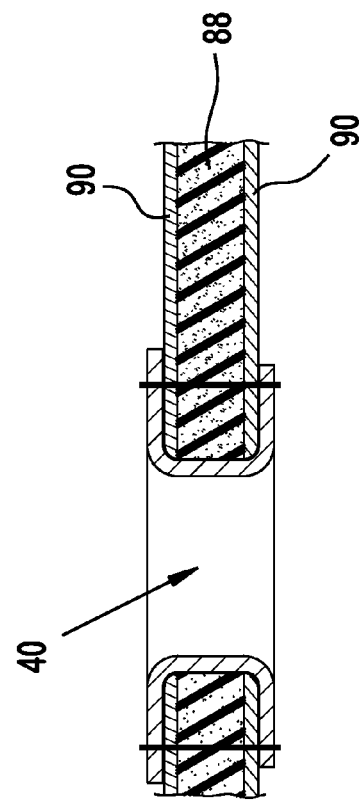
FIG. 28 illustrates cross-sectional views of the splint of FIG. 26; one of ordinary skill in the art will appreciate from this disclosure that Tenoplast tape may or any suitable material may be substituted for another material such as Neoprene and the splint may be cut and shaped without wrapping and the outer layer would consist of a semiporous material like Neoprene and this would support and contain the inner layers replacing the tape and wrapping semielastic outer layers.

As shown in FIG. 26, a second embodiment of the splint 30 of the present invention uses a single cushioning layer 88 (or padding layer) with the reinforcement strut 58 placed thereon and the foam pad 86 placed on opposite side of the splint 30. It is preferable that the splint is wrapped in neoprene 90 (or a covering layer).

In other words the present invention may be directed to a splint 30 configured for use on a hand, a wrist, and a forearm of a person including a padding layer. A reinforcement strut 58 may is positioned on and/or in the padding layer 88. The reinforcement strut can be configured to deform under use of the hand by the person and then return to a predetermined position once the hand is not in use. A covering layer 90 may surround the padding layer and the reinforcement strut. The reinforcement may be formed by an elongated polymer comprising a preheated thermoplastic stay. The reinforcement strut may deform from the predetermined position when more than four pounds or more of force is exerted on an end thereof and then may return to the predetermined position when the force is less than four pounds. Alternatively, the reinforcement strut 58 may be designed to operate within the splint 30 as a leaf spring. The reinforcement strut may be designed to temporarily deform when more than ten pounds of pressure is applied proximate an end thereof. For example when a palm of a user moves relative a plane of a surface of the forearm along which the strut 58 is positioned to cause the ends of the strut 58 to have a force exerted thereon which may bend the strut inwards or outwards from the perspective of the user. Alternatively, the reinforcement strut 58 may be designed to temporarily deform when more than five pounds of pressure is applied proximate an end thereof. Alternatively, the reinforcement strut 58 may be designed to temporarily deform when more than two pounds of pressure is applied proximate an end thereof. Those of ordinary skill in the art will appreciate from this disclosure that the amount of force necessary to deform or just bend the strut 58 can be varied without departing from the scope of the present invention. Alternatively, the strut 58 can be design to provide dampening resistance to motion similar to a shock absorber while allowing a range of motion of approximately ninety degrees (from a maximum cocked up position to a maximum cocked down position). Alternatively, the strut 58 can be design to provide dampening resistance to motion similar to a shock absorber while allowing a range of motion of approximately fifty degrees (from a maximum cocked up position to a maximum cocked down position). Those of ordinary skill in the art will appreciate from this disclosure that the range of motion can be varied without departing from the present invention.

The dynamic custom splint of the present invention is preferably a tape splint that allows optimal position for healing and decrease in inflammation and swelling. It also allows proper positioning of nerve and tendon structures for healing and are made specifically to address the issues at hand with respect to tendinitis and perineural inflammation. These splints also are ideal for improved compliance and limit problems such as chafing, increased symptoms due to non ideal positioning and allow also for perfect conforming to allow better soft tissue adaptation and healing.

The splint preferably includes meets the following basic criteria:
1. fits comfortably
2. adheres to bio-mechanical principles
3. can be applied independently by the patient
4. is esthetically pleasing
5. meets the needs of the patient without to great a disruption of life style (e.g personal care, vacation, avocation)
6. The splint is designed to be used under daytime and night conditions
7. The donning of the splint is in a specific manner 8. The velcro straps are opened and the hand is placed in the splint and the thumb slid through the opening for the same. The splint is then wrapped around the hand, forearm and wrist so that it fits comfortable but not too snugly 9. The straps are then fastened, using the velcro in standard manner to seal the splint about the extremity. These straps are then adjusted to provide a fit that is supportive and yet not too tight. Each individual strap can be loosened or tightened according to activity and or with adjustment to any swelling or comfort desired The splint cam be worn with activity and at night to provide support but also with activity it provides intermittent compression and the addition of heat to the flexor tendons and the median nerve itself at the carpal canal by design and the intermittent variable pressure placed dynamically about the volar forearm musculoligamentous structures. This provides a vehicle to move the fluid from these structures, actually pumping the swelling and edematous fluid out of the area of pathology, to allow decrease in inflammation and irritation of these structures as well as the surrounding soft tissues and prevent the formation of pathologic scar tissue.

The device may be removed for bathing, light activities and rest and will be used as defined by the treating medical practitioner and or therapist.

This splint can be designed as a thumb spica as well, incorporating the thumb to protect the basal joint and help to prevent the development of arthritis it also prevents progression of arthritis in individuals that already have arthritis present.

To fabricate this device an initial layer may be molded of deep padding. The splint can be molded about the thumb designing the perfect opening for the thumb yet support for the basal joint and MP joint as needed and desired. This opening is padded to protect for abrasion and excessive tightness at the base of the thumb to protect the tendons and the neuro vascular structures such as the digital nerves. Next a second supportive layer may be made using a layer of tape. The dynamic semi elastic strut may be added to maintain the wrist in 0 degrees neutral. A second layer if the tape can added next to incorporate the strut and add rigidity as desired to the splint. Next a layer of padding is added Once formed a final outer layer may be applied. Once all layers are done the splint cam sealed to prevent unraveling and protect it from water damage.

It is recognized by those skilled in the art, that changes may be made to the above described embodiments without departing from the broad inventive concept thereof. It is understood, therefore, that this invention is not limited to the particular embodiments disclosed, but is intended to cover all modifications which are within the spirit and scope of the invention as defined by the appended claims and/or shown in the attached flowcharts.

What is claimed is:

1. A method of manufacturing a custom splint adapted for a person configured for use on a hand, a wrist, and a forearm of the person, comprising:
    applying a stockinette to the wrist and the forearm, the stockinette being configured to form a first layer of the custom splint;
    wrapping a fabric material about the first layer of the custom splint to form a second layer of the custom splint configured to provide bulk to the custom splint and to protect the wrist and the forearm of the person covered by the custom splint;
    while maintaining a neutral position of the wrist, wrapping a semi-elastic woven stretch material around the second layer of the custom splint to form a third layer of the custom splint configured to provide spring and breathability to the custom splint; and
    positioning a reinforcement strut on the third layer and securing the reinforcement strut thereto proximate to the wrist such that the reinforcement strut is configured to facilitate maintaining the wrist in the neutral position.

2. The method of claim 1, wherein the step of positioning the reinforcement strut further comprises the reinforcement strut being formed by an elongated polymer member that is generally aligned parallel to a longitudinal axis of the custom splint and configured to extend over the wrist area of the custom splint to facilitate maintaining the wrist in a desired position when the custom splint is worn.

3. The method of claim 2, wherein the step of positioning the reinforcement strut further comprises the reinforcement strut being formed by the elongated polymer member comprising a preheated thermoplastic stay.

4. The method of claim 2, further comprising the step of wrapping semi-elastic tape over the reinforcement strut and the third layer of the custom splint to secure the position of the reinforcement strut within the custom splint and to form a fourth layer of the custom splint configured to provide additional support for the forearm and the hand.

5. The method of claim 4, wherein the step of wrapping the fabric material further comprises the fabric material comprising cotton.

6. The method of claim 5, wherein the step of wrapping the fabric material further comprises the fabric material being a cotton cling material.

7. The method of claim 6, further comprising the step of taping the ends of the cotton cling material to secure it in place over the stockinette.

8. The method of claim 7, wherein the step of applying the stockinette further comprises the stockinette being configured to cover at least three fourths of the forearm of the person.

9. The method of claim 8, wherein the step of wrapping the fourth layer further comprises wrapping a porous, elastic tape around the reinforcement strut and the third layer to form the fourth layer providing additional bulk to the custom splint and to provide support for the forearm and the hand.

10. The method of claim 9, wherein the steps of wrapping the first layer, the second layer, the third layer, and the fourth layer of the custom splint include covering at least a portion of a thumb.

11. The method of claim 10, further comprising marking a path along an outer surface of the custom splint from approximately the third metacarpophalangeal (MCP) joint down the middle of the custom splint and cutting along the mark to enable removal of the custom splint, cutting along the path resulting in two vertical edges in the custom splint.

12. The method of claim 11, further comprising marking areas to be cut around the thumb and transverse palmar crease.

13. The method of claim 12, further comprising cutting the custom splint along the areas marked around the thumb and transverse palmar crease.

14. The method of claim 13, further comprising placing a soft woven fabric with a piled texture on one side along a thumb hole in the custom splint to protect against abrasion.

15. The method of claim 14, further comprising the step of folding strips of the porous, elastic tape around the two vertical edges of the custom splint, the folds in the strips being along the longitudinal axis thereof.

16. The method of claim 15, wherein the step of positioning the reinforcement strut further comprises the reinforcement strut formed by the elongated polymer member comprising a preheated thermoplastic stay.

17. The method of claim 1, wherein the step of positioning the reinforcement strut further comprises the reinforcement strut deforming from a predetermined position when more than four pounds or more of force is exerted on an end thereof and then returns to the predetermined position when the force is less than four pounds.

* * * * *